(12) United States Patent
Gaudet

(10) Patent No.: US 9,063,552 B2
(45) Date of Patent: *Jun. 23, 2015

(54) ELECTRONIC CONTROLLER FOR SYRINGE PISTON CONTROL

(71) Applicant: Teneo Innovations Inc., Laval (CA)

(72) Inventor: Martin Gaudet, Laval (CA)

( * ) Notice: Subject to any disclaimer, the term of this patent is extended or adjusted under 35 U.S.C. 154(b) by 228 days.

This patent is subject to a terminal disclaimer.

(21) Appl. No.: 13/764,910

(22) Filed: Feb. 12, 2013

(65) Prior Publication Data

US 2013/0146615 A1    Jun. 13, 2013

Related U.S. Application Data

(63) Continuation-in-part of application No. 13/085,834, filed on Apr. 13, 2011, now Pat. No. 8,403,888.

(60) Provisional application No. 61/324,479, filed on Apr. 15, 2010.

(51) Int. Cl.
  *A61M 37/00* (2006.01)
  *G05D 13/02* (2006.01)
  *A61M 5/145* (2006.01)
  *A61M 5/178* (2006.01)

(52) U.S. Cl.
  CPC ............. *G05D 13/02* (2013.01); *A61M 5/1452* (2013.01); *A61M 5/1782* (2013.01); *A61M 2205/14* (2013.01); *A61M 2205/50* (2013.01); *A61M 2205/502* (2013.01); *A61M 2205/70* (2013.01)

(58) Field of Classification Search
  USPC .................... 604/151, 154–156; 222/63, 333; 417/18, 415
  See application file for complete search history.

(56) References Cited

U.S. PATENT DOCUMENTS 8,403,888 B2 * 3/2013 Gaudet .......................... 604/154

* cited by examiner

*Primary Examiner* — Quynh-Nhu H Vu
(74) *Attorney, Agent, or Firm* — Larson & Larson, P.A.; Justin P. Miller; Patrick A. Reid

(57) ABSTRACT

An electronic controller module for controlling outward movement of the piston comprises an input/output port and a processor module. The processor module determines a prescribed movement speed and sends a motor command via the port at an initial motor speed. The motor causes the outward movement. The port receives speed measurements. The processor module attempts to match the measurements to a prescribed speed by sending successive motor commands via the port.

17 Claims, 18 Drawing Sheets

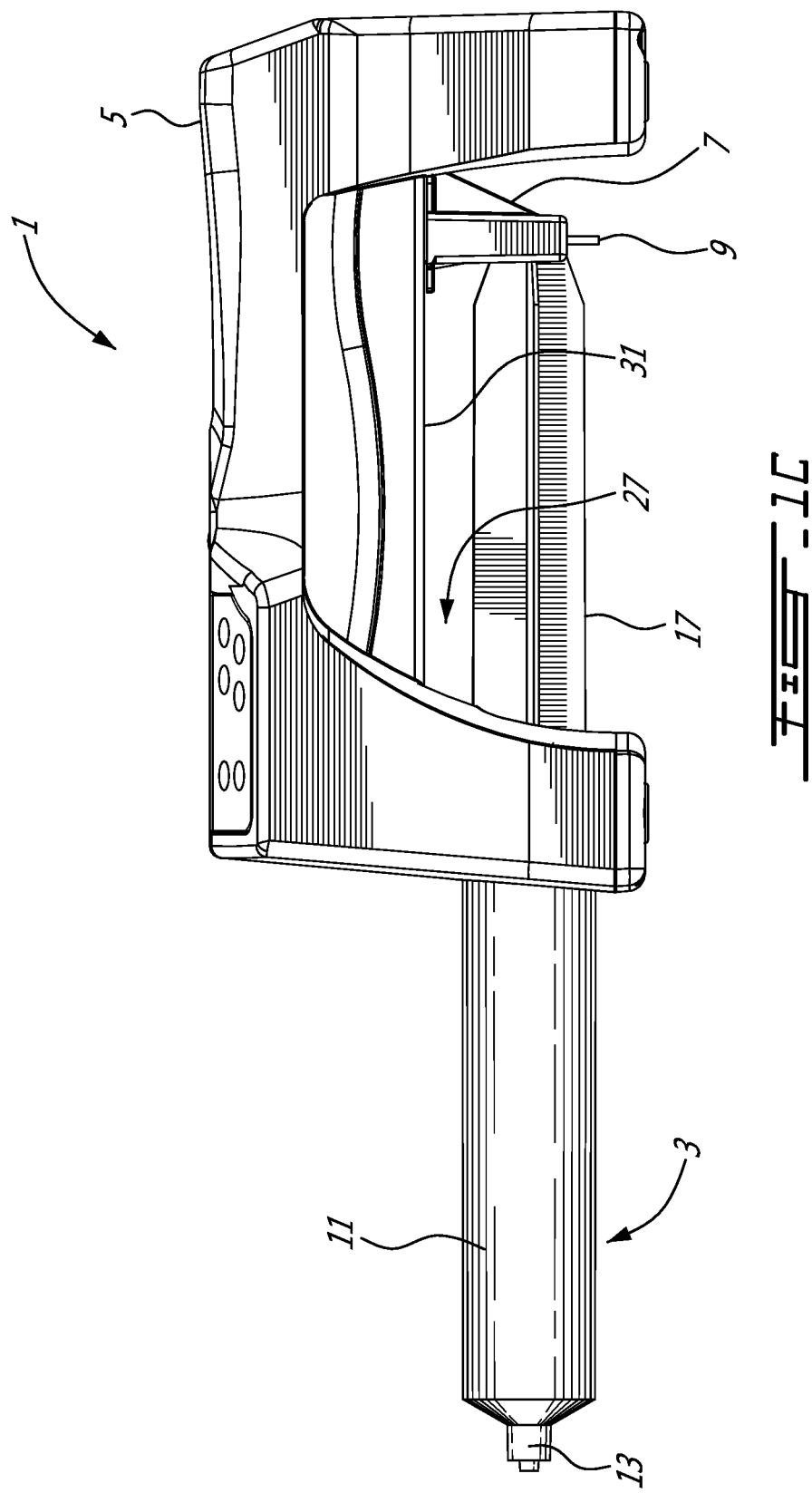

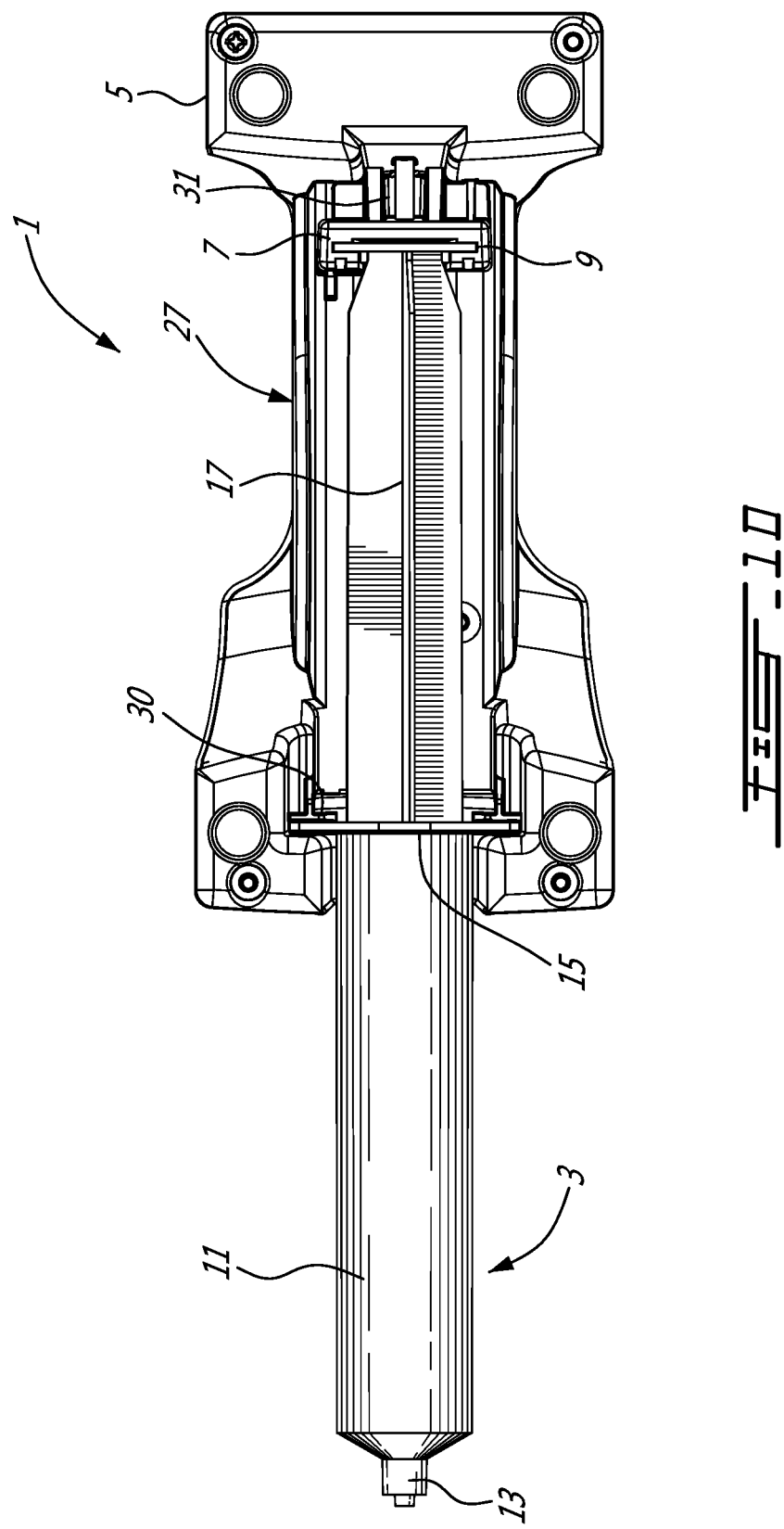

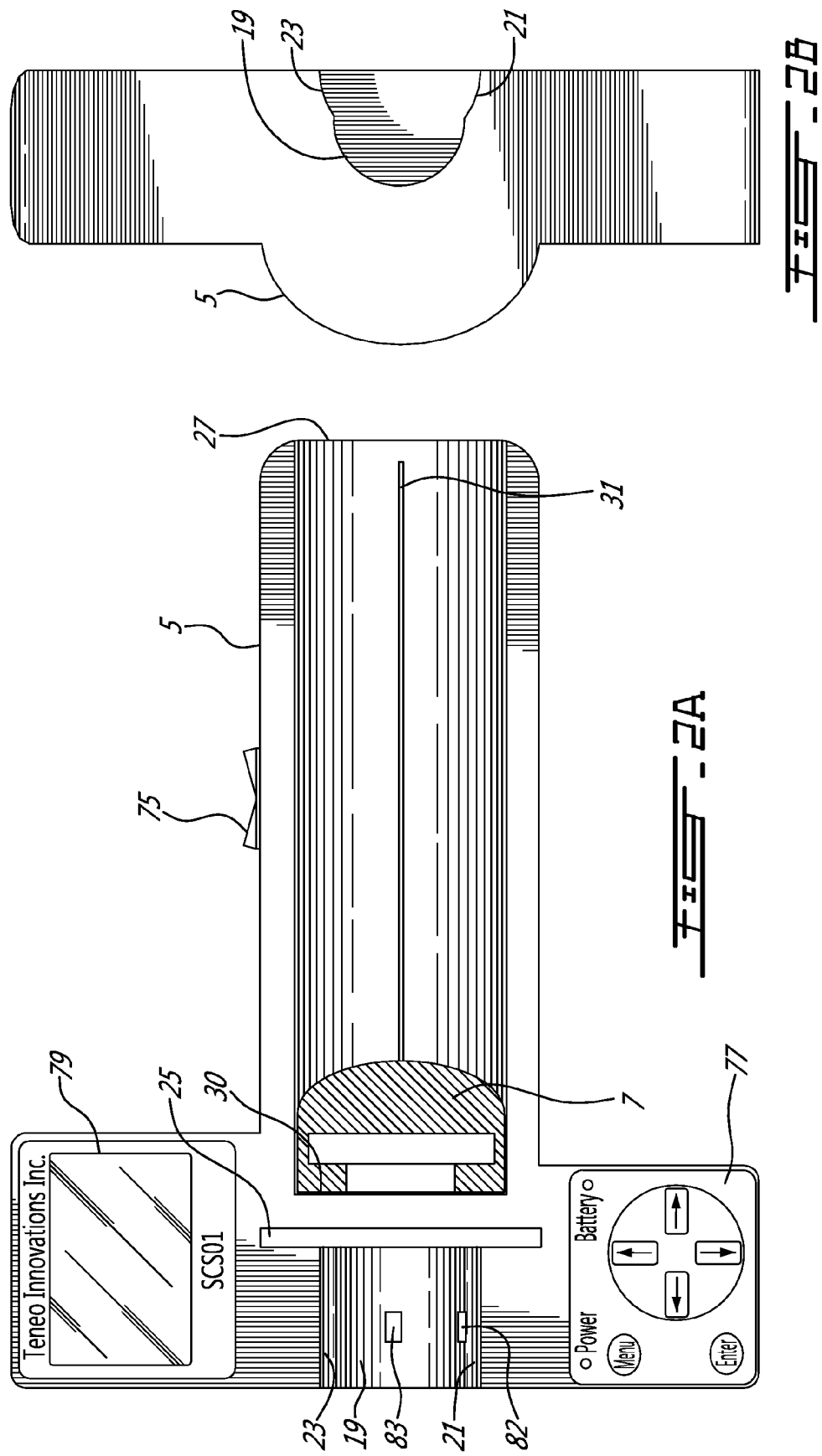

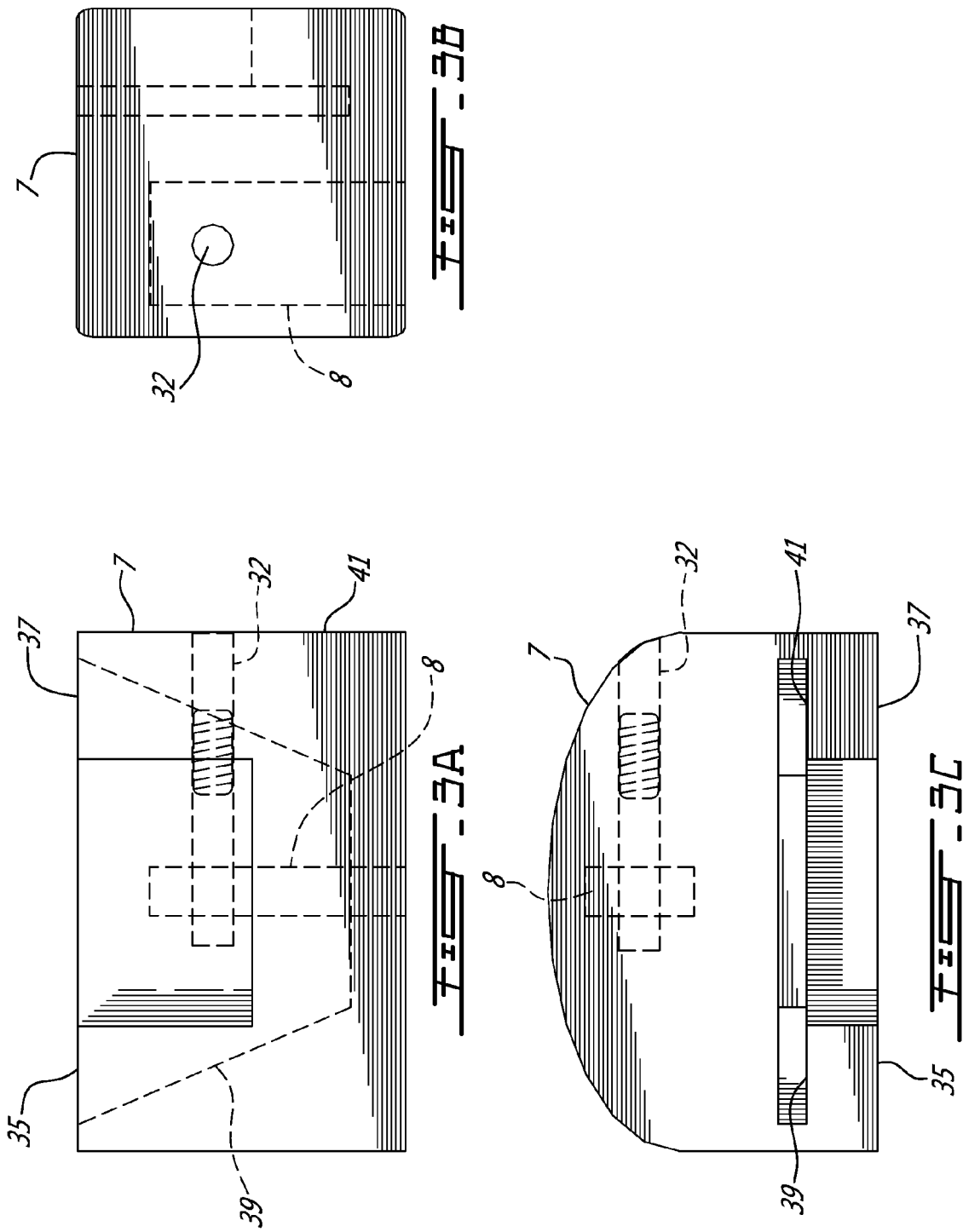

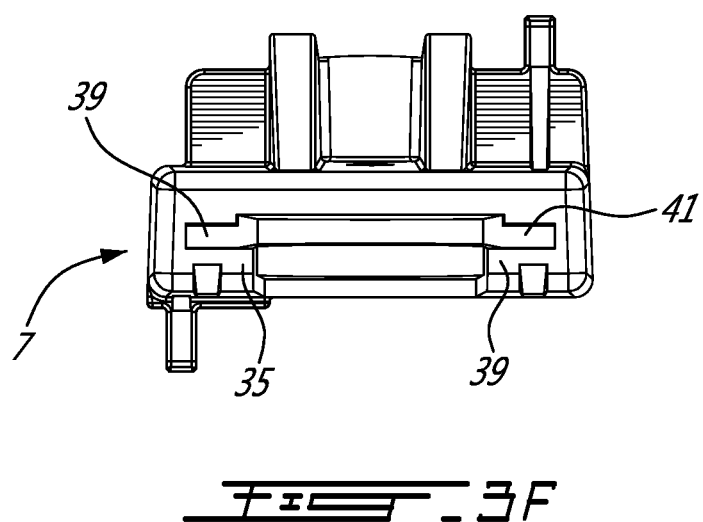

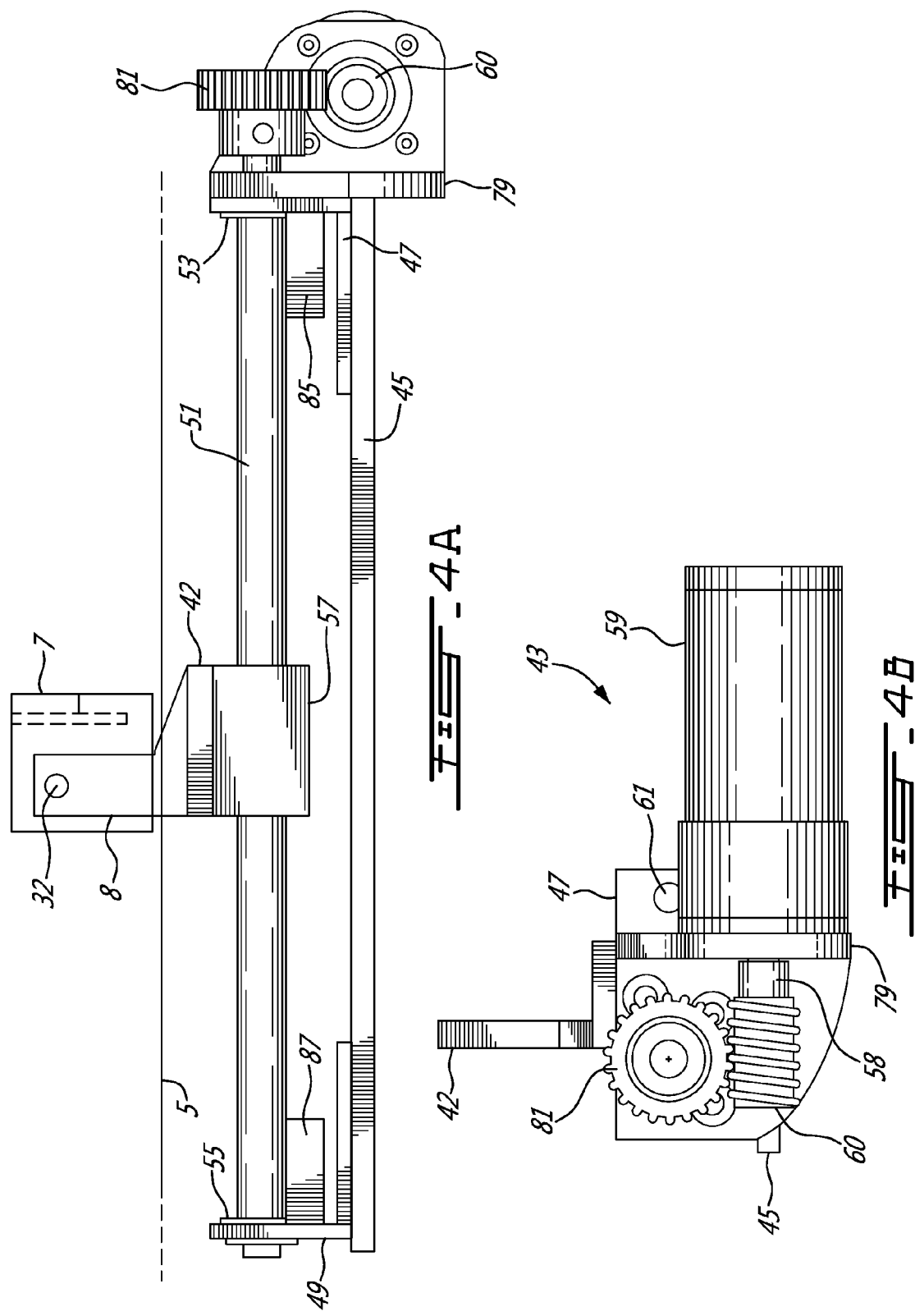

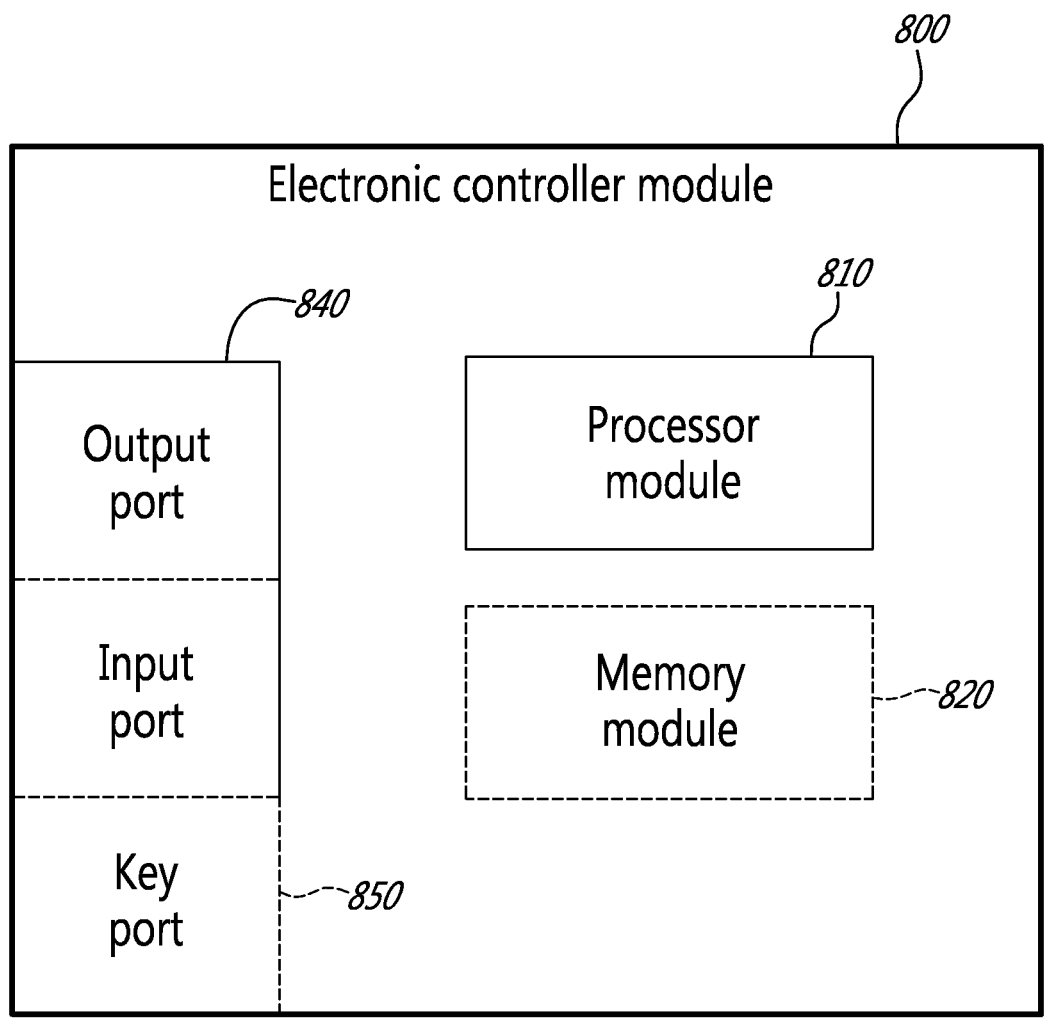

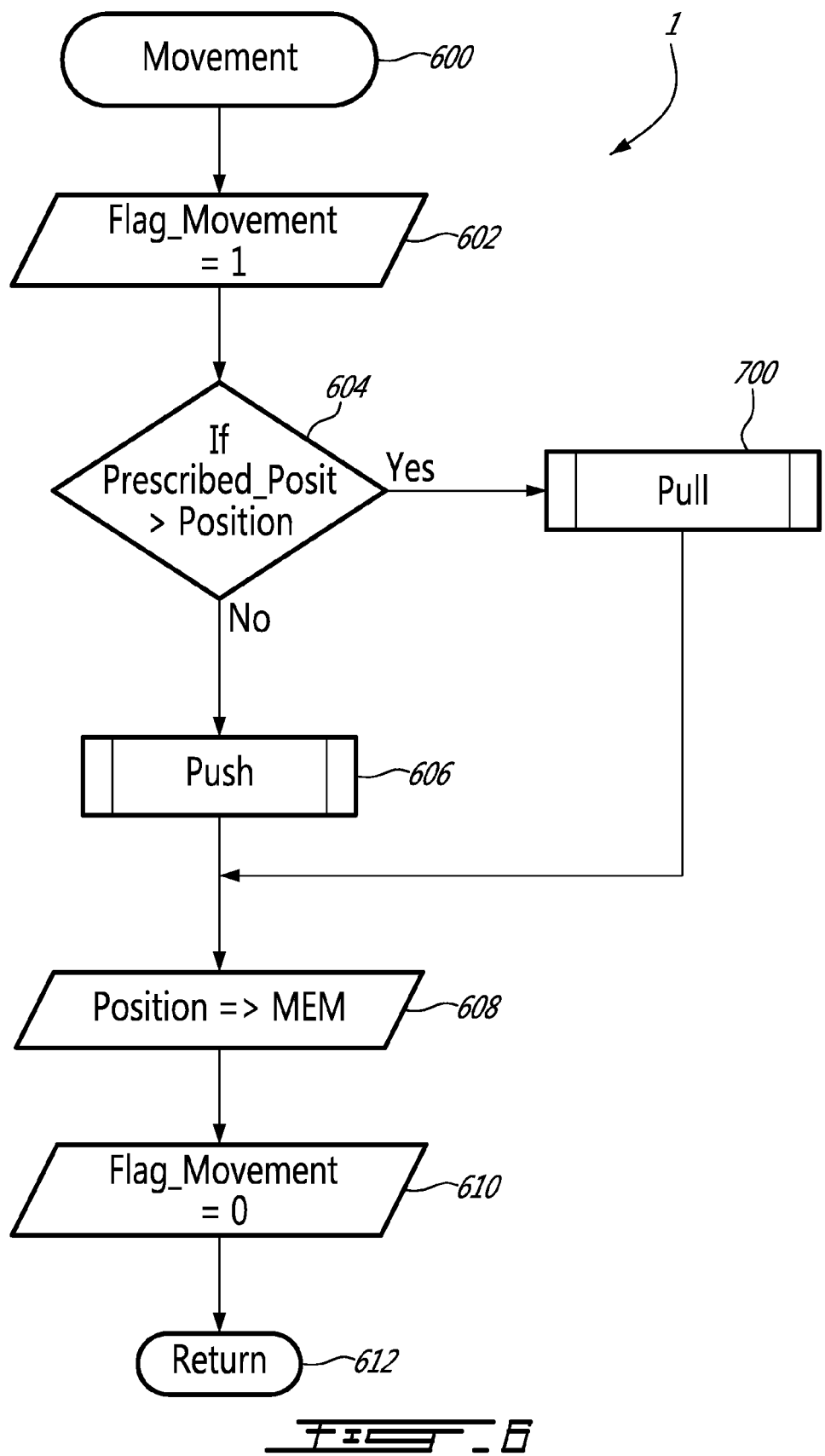

US 9,063,552 B2

ELECTRONIC CONTROLLER FOR SYRINGE PISTON CONTROL

PRIORITY STATEMENT UNDER 35 U.S.C §.119(e) & 37 C.F.R. §.1.78

This non-provisional patent application claims priority based upon the prior U.S provisional patent applications titled "MECHANISM TO ASSIST SYRINGE MANIPULATION", application No. 61/324,479, filed Apr. 15, 2010, in the name of Martin Gaudet, and is a continuation-in-part of U.S. patent application Ser. No. 13/085,834, filed Apr. 13, 2011, titled "Device And Electronic Controller For Syringe Piston Control."

TECHNICAL FIELD

This invention relates to a control system for syringe. More particularly, the invention relates to a device for controlling displacement of a syringe piston.

BACKGROUND

Manipulation of syringes whose volume may vary for example between 30 and 60 ml presently constitutes a source of injuries in hospitals or research centers. It has been realized that retractions and thrusts of syringes may require sufficient strength in the hands and wrists of an operator to result in potential injuries. These operations are especially demanding when performed in a sterile environment (such as a sterile hood), which often requires the operator to work arms extended, with gloved hands. Repetition of these operations may result, for instance, in tendinitis. In addition, these operations are time consuming, which means that preparation, for instance, of intravenous medicines may be longer than can be ideally afforded.

Considering the foregoing, a need exists to provide better syringe control.

SUMMARY

A first aspect of the present invention is directed to a device for controlling displacement of a syringe piston within a syringe that comprises a hollow barrel to contain a fluid. The barrel has a finger flange at an inner end thereof, the syringe piston being slidably engaged in the hollow barrel and having a thumb rest at an outer end thereof. The device comprises a handheld outer casing, first and second engagement means. The first engagement means (e.g., a finger flange retainer) is formed exteriorly of the casing to fixedly engage the finger flange. The second engagement means (e.g., thumb rest retainer) is slidably movable on a first axis relative to the outer casing and adapted to engage the thumb rest. The device further comprises means disposed within the outer casing (e.g., a mechanical driver) to cause the second engagement means to move along the first axis, causing the piston to move outwardly within the hollow barrel.

Various options related to the device are provided in the next paragraphs. The means disposed within the outer casing to cause the second engagement means to move along the first axis may further cause the piston to move inwardly within the hollow barrel. The outer casing may further comprise a rest means allowing the syringe to sit on an upper face of the casing. The rest means may further be adapted to receive syringes of various diameters. The rest means may also further comprise an elongated circular recess formed at one end of the outer casing, the recess having a radius corresponding to the diameter of the hollow barrel. In addition the circular recess may also include a pair of oppositely disposed curved cut out portions adapted to permit a syringe with a hollow barrel of larger diameter to sit in the circular recess.

Other options of the device include that the first engagement means comprises a transverse slit formed in the outer casing at an inner end of the circular recess and adapted for insertion of the finger flange therein to fix the syringe relative to the outer casing. The outer casing may also be formed with a longitudinal channel along the first axis which extends from one end of the casing to the inner end of the circular recess, a slot being formed at the bottom of the channel and extending along the first axis. The second engagement means may also further comprise a claw adapted to engageably receive the thumb rest, the claw being slidably engaged in the channel and operatively connected to the interiorly disposed means. The claw may be shaped as a plate having a pair of oppositely disposed holding wings to receive and hold the thumb rest. The wings may be inwardly beveled to hold pistons and thumb rests of various diameters.

Yet other options of the claw comprise a leg downwardly extending from a bottom portion of the vertical plate and centrally thereof, the leg extending through the slot to connect with the interiorly disposed means. Alternatively, the interiorly disposed means may also comprise a shaft extending upwardly through the slot to connect with the claw. Rubber strips may be provided in the slot to isolate the interiorly disposed means alternatively, or in addition, a first rubber-encased spring may be provided in the slot between the one end of the casing and the claw and a second rubber-encased spring may also be provided in the slot between the claw and the inner end of the circular recess. The first and second rubber-encased springs, if present, are used in isolating the interiorly disposed means.

Optionally, the interiorly disposed means may comprise a rigid structure disposed inside the outer casing. The interiorly disposed means may also comprise a lead screw mounted on the rigid structure in alignment with the first axis, a flange nut assembly mounted over the lead screw to move therealong without rotation relative to the rigid structure as the lead screw is rotated, a driving peg fixed to the flange nut assembly and connected to the second engagement means. The lead screw may be operatively connected to a motor through at least one gear. The motor may have a shaft inserted into a worm screw, a spur gear being fixedly mounted at one end of the lead screw such that the spur gear meshes with the worm screw to operate the lead screw. The motor may be operable in both directions and may have an encoder to measure rotations.

The device may also optionally comprise a flip-flop button mounted on the outer casing and operable to control the second engagement means. The rigid structure may also comprise a monitoring rod parallel to the lead screw. The flange nut assembly may be engaged over the monitoring rod to prevent rotation of the flange nut assembly when the lead screw is rotated. The lead screw may be mounted on the rigid structure by means of a pair of ball bearings supported at both ends of the lead screw. The rigid structure may also have an inner end wall and an outer end wall. The lead screw could then be mounted on top of the inner end wall and the outer end wall through ball bearings while the inner end wall is disposed to allow for calibrating the syringe at a zero value and the outer end wall is disposed to prevent the piston from movably extending outside the hollow barrel.

The device may also optionally further comprise a keyboard and a screen disposed on a face of the outer casing to program the device and to monitor its operation. The outer casing may also be designed to be handheld and the device may be battery operated in a sterile environment.

A second aspect of the present invention is directed to an electronic controller module for controlling displacement of a syringe piston within a syringe that comprises a hollow barrel to contain a fluid. The syringe piston is slidably engaged in the hollow barrel. The electronic controller causes an outward movement of the syringe piston within the barrel. The electronic controller module comprises an input/output port and a processor module. The processor module is used for determining a prescribed speed of the outward movement. The processor module sends an initial motor command via the output port to activate a motor at an initial motor speed. The motor is operatively connected to the syringe piston to cause the outward movement. The input port receives speed measurements. The prescribed speed and the speed measurements may be stored in a memory module of the electronic controller module. The processor module thereafter attempts to match the prescribed speed based on the speed measurements by sending successive further motor commands via the output port. Each further motor command comprises a further motor speed. The electronic controller module is within a handheld syringe control system that may be battery operated in a sterile environment.

Various options related to the electronic controller are provided in the next paragraph. For instance, a prescribed end position of the outward movement may be stored in a memory unit. The input port may also further receive position measurements of the syringe piston. The processor module may thus send a final motor command via the output port to stop the motor once at least one of the position measurements matches the prescribed end position. The processor module may be able to divide the prescribed speed by a factor (e.g., reduce speed by two-fold) once at least one of the position measurements is within a range from the prescribed end position (e.g., when the position measurement is within the range of 1 cm, the speed is divided by 3, when the position measurement, once converted to volume, is within a range of ⅛ of the total volume required, the speed is divided by 10, etc.). The prescribed speed and/or the prescribed end position may be received via from a key port.

Optionally, the processor module may further receive a command to cause an inward movement of the syringe piston within the barrel. The processor module may thus send an inward motor command via the output port to activate the motor at an inward motor speed. The motor may be operatively connected to the syringe piston to cause the inward movement. The processor module may also send a stop motor command via the output port once at least one of the position measurements matches an empty position.

BRIEF DESCRIPTION OF THE DRAWINGS

Further features and advantages of the present invention will become apparent from the following detailed description of preferred embodiments, taken in conjunction with the annexed drawings, in which:

FIGS. 1B, 1C and 1D are respective top, front and bottom views of an exemplary device in accordance with the present invention, FIGS. 1A to 1D being referred together as FIG. 1;

FIG. 2A is a front view of the exemplary device illustrated in FIG. 1A without a syringe adapted to be used therewith;

FIG. 2B is a left side view of the device illustrated in FIG. 1A without the syringe adapted to be used therewith;

FIG. 3A is a front view of an exemplary claw used to engage a thumb rest of a syringe piston in accordance with the present invention;

FIG. 3B is a left side view of the exemplary claw used to engage the thumb rest of the syringe piston;

FIG. 3C is a top view of the exemplary claw used to engage the thumb rest of the syringe piston;

FIG. 3F is a top view of the exemplary claw used to engage the thumb rest of the syringe piston, FIGS. 3A to 3F being referred together as FIG. 3;

FIG. 4A is a front view an exemplary mechanical assembly of the exemplary device according to the invention in accordance with the present invention;

FIG. 4B is a right side view of the exemplary mechanical assembly of the exemplary device according to the invention;

FIG. 5 is a modular representation of an exemplary electronic controller module in accordance with the present invention;

FIG. 6 is a flowchart of an exemplary method to control movement in accordance with the present invention;

DETAILED DESCRIPTION

The present invention, as described with reference to exemplary embodiments hereinafter, provides, for instance, a handheld system to control syringe actions without manually actuating the syringe's piston. The present invention, as described with reference to exemplary embodiments hereinafter, also provides, for instance, a control system for a motor that actuates a syringe's piston within a handheld syringe control system.

Figure 1A:
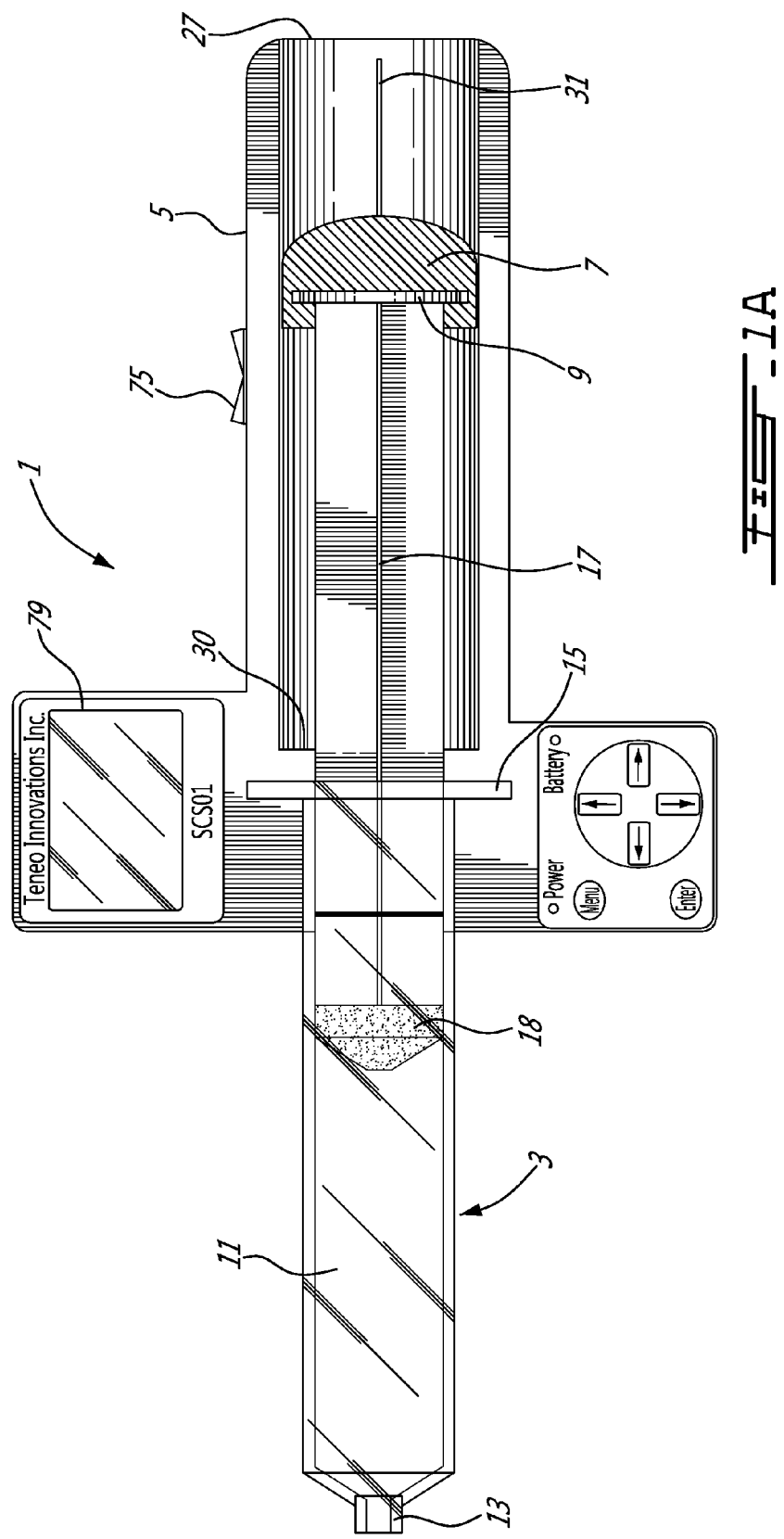
FIG. 1A is a front view of an exemplary device in accordance with the present invention.
Figure 1B:
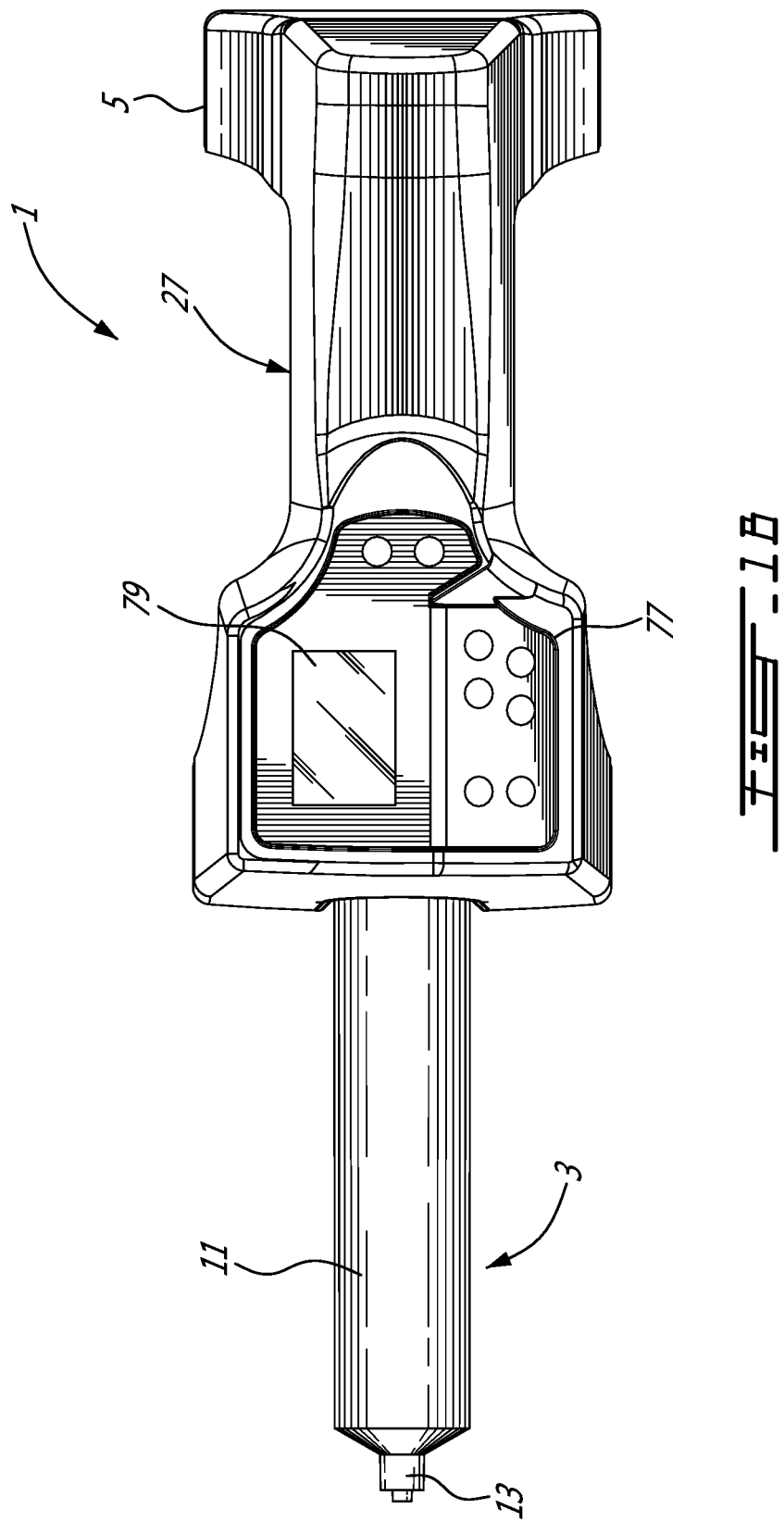
Figure 2C:
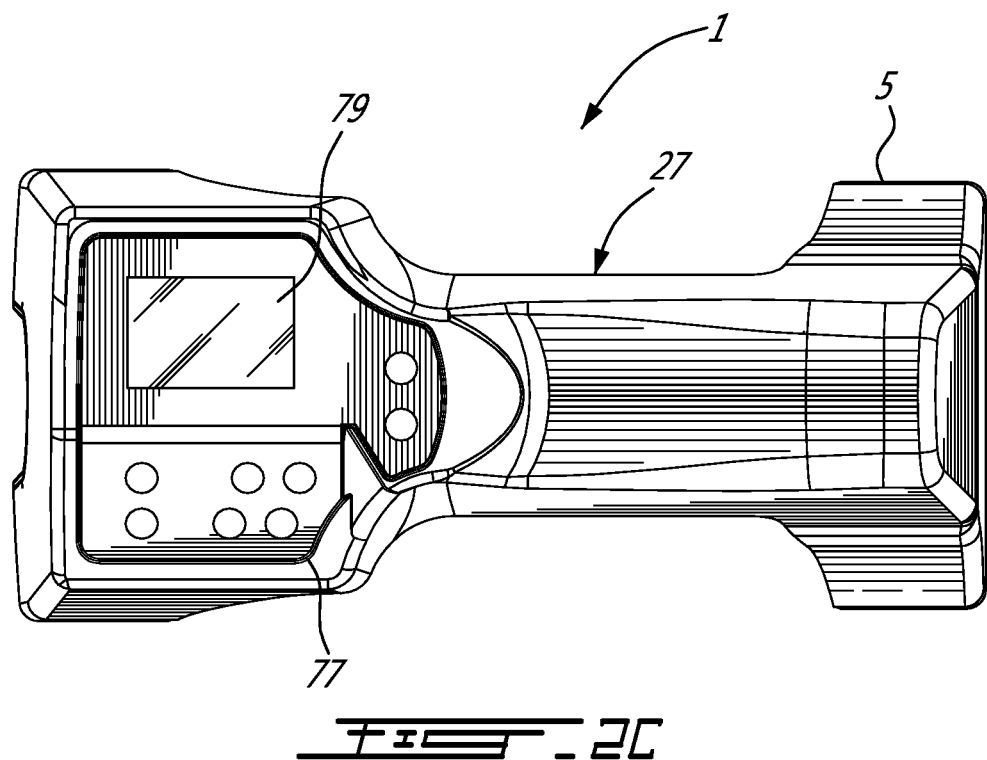
FIGS. 2C, 2D, 2E and 2F are respective top, front, bottom and left side views of the exemplary device illustrated in FIGS. 1B to 1D without a syringe adapted to be used therewith, FIGS. 2A to 2F being referred together as FIG. 2.
Figure 2D:
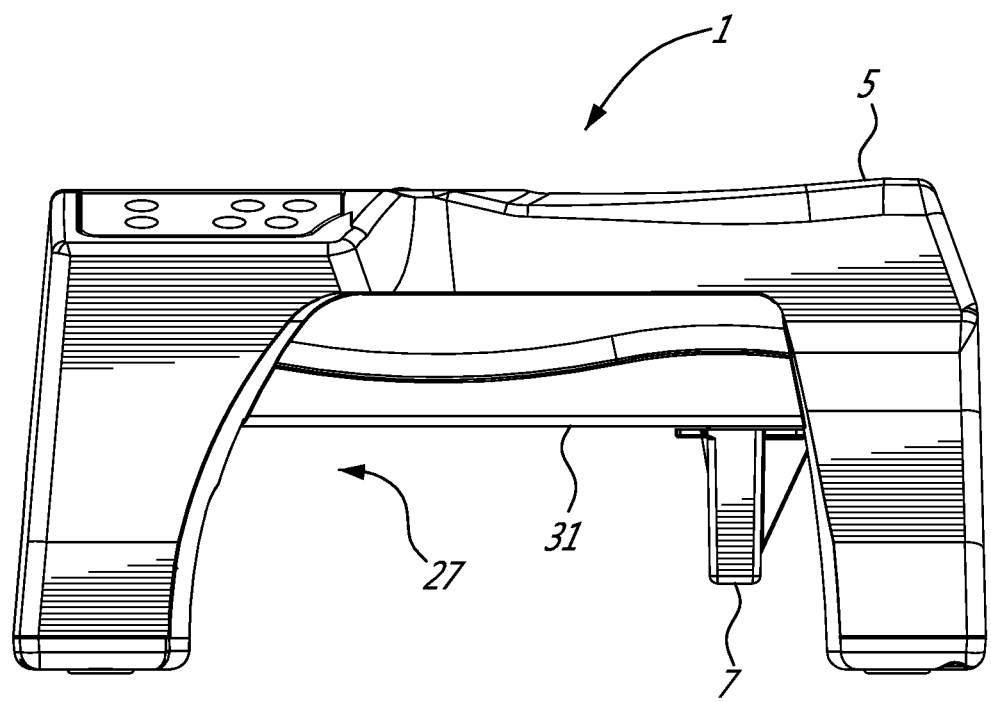
Figure 2E:
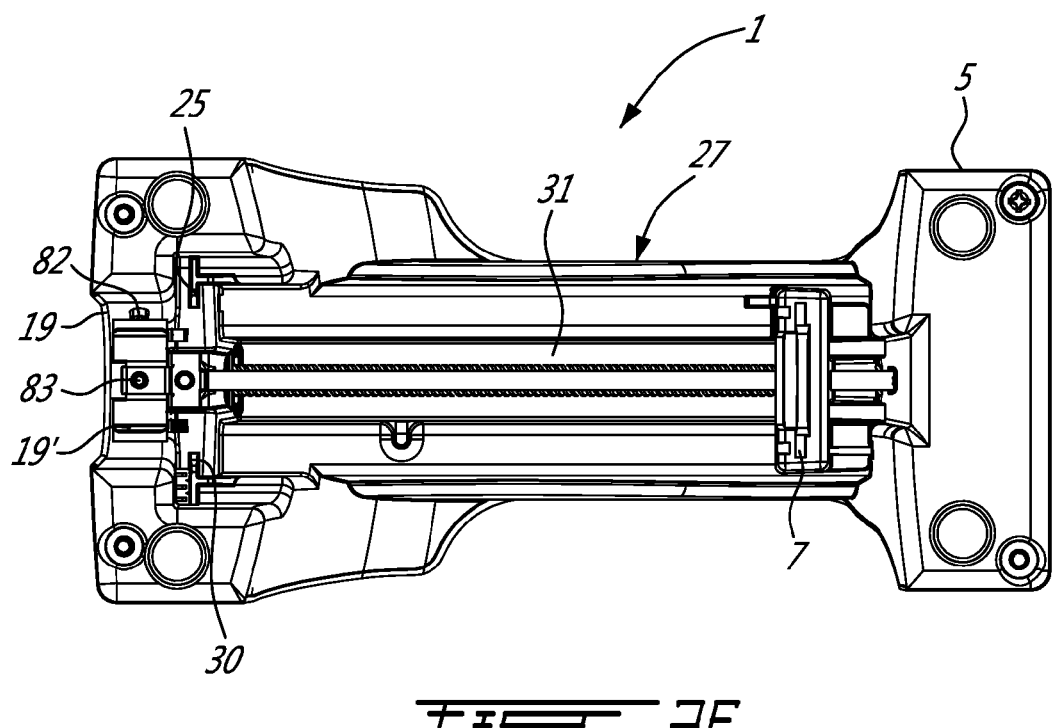
Figure 2F:
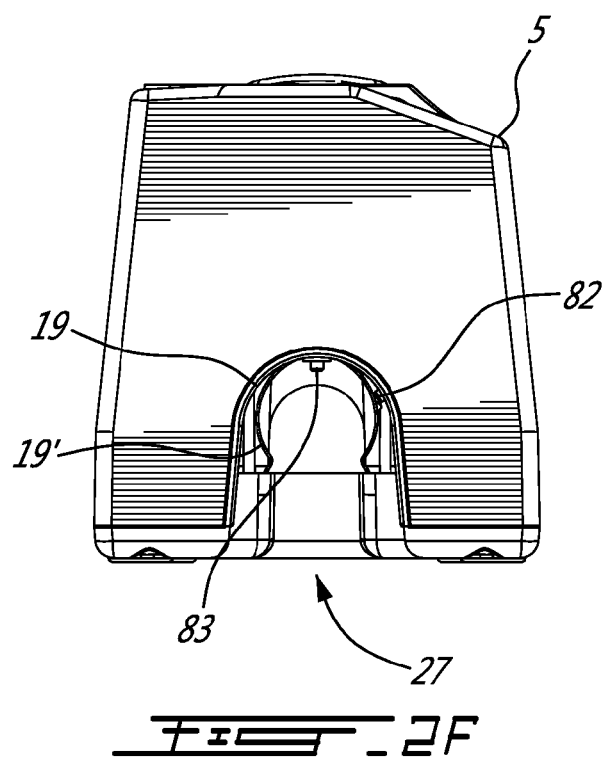

Reference is now made to drawings, in which FIG. 1 shows views of an exemplary device 1 in accordance with the present invention. It will be noted that the device 1 capable of controlling the inward and outward displacement of the piston of an exemplary syringe 3 generally comprises an outer casing 5 and a claw 7 for engaging the thumb rest 9 of piston rod 17. The device 1 may engage the syringe's 3 piston in a manner to counteract any resistance caused by a fluid to be injected, such as a high viscosity liquid, using the syringe 3. The device 1 may further engage the syringe's 3 piston to expel amounts of the above fluid in a controlled manner.

The exemplary syringe 3 is of the type well known to those skilled in the art, which normally consists of a hollow barrel 11 which is terminated by a hub 13 adapted to, for instance, receive a tube (not shown) or to mount a needle (not shown), which can be chosen from those intended for a variety of specific uses, as is well known to those skilled in the art. Exemplary volumes addressed by the present invention are 30 ml and 60 ml, but skilled readers will readily recognize that the present invention may use readily available syringes of various volumes, or custom-made syringes of various volumes, without affecting the present invention.

The syringe 3 also comprises a finger rest 15 disposed and mounted at the inner end of hollow barrel 11, and a piston rod 17, which slides in and out of the hollow barrel 11 and is terminated by a sealing bulb 18 at the outer end thereof.

The present invention provides a handheld outer casing 5, which will now be described in detail with particular reference to FIGS. 1, 2, 3 and 4. More specifically, the casing 5 may efficiently be held in one hand and may have the general shape as illustrated in FIGS. 1 and 2, although any other suitable shape, which can be designed by one skilled in the art is understood to be within the scope of the present invention (e.g., the casing 5 could also be generally prismatic). In practice, the casing 5 can be shaped to receive 30 or 60 ml syringes, although its shape and size can be modified according to various needs and the choice of the skilled artisan. In addition, it should be noted that the device 1 according to the present invention is such that the piston should be actuated within predefined precision, and may advantageously be actuated so as to counteract resistance caused by fluid intended to be manipulated through the syringe 3.

The casing 5 may be made of a material, which allows its user to have a good grip when handling the device 1. The material may, for instance, be made of a substance, generally a plastic material, which is resistant to cleaning and disinfecting fluid, such as an alcohol, which can used to disinfect the device 1. This, for instance, can be especially advantageous if the device 1 is used in a sterile environment (such as a sterile hood).

At one end, the casing 5 is formed with a half circular recess 19 as particularly illustrated FIG. 2. The half circular recess 19 is sufficiently long to permit a substantial portion of hollow barrel 11 to be well received therein. The half circular recess 19, in the illustrated embodiment of FIGS. 2A and 2B, is dimensioned to receive a 30 ml syringe. In order to also be adapted to receive a 60 ml syringe, the half circular recess 19 is formed with a pair of oppositely disposed curved cut out portions 21, 23 as shown particularly in FIG. 2. To ensure that once the syringe 3 is disposed in the half circular recess 19, and stays well seated therein, there is provided a transverse slit 25 as particularly shown in FIG. 2, immediately at the end of the circular recess 19. The transverse slit 25 is just wide and deep enough to engage finger rest 15 in the particular manner shown in FIG. 1. The half circular recess 19, in the illustrated embodiment of FIGS. 2C to 2F, is dimensioned to receive a 60 ml syringe. In order to also be adapted to receive a 30 ml syringe, the half circular recess 19 comprises a clip 19' as shown particularly in FIGS. 2E and 2F, which also ensures that once the syringe 3 is disposed in the half circular recess 19, and stays well seated therein.

The casing 5 also comprises a longitudinal channel 27 as illustrated in FIGS. 1 and 2. The channel 27 is dimensioned to slidably receive the claw 7 when the latter is positioned perpendicular to the channel 27. The claw 7 will be described in detail later when the description of longitudinal channel 27 is completed, with particular reference to FIG. 3. As illustrated in FIGS. 1 and 2, the longitudinal channel 27 extends from the end of the casing 5 opposite the circular recess 19 to a stop 30 provided at the end of circular recess 19. At the bottom of the channel 27, there is provided a slot 31, which extends short of both ends of the channel 27 as shown in FIGS. 1 and 2 and downwardly extends into the interior of the casing 5 (not shown). It will also be noted that the slot 31 is wide enough to allow a mechanical connection to be made from the casing 5 towards the claw 7 or from the claw 7 towards the casing 5.

Figure 3E:
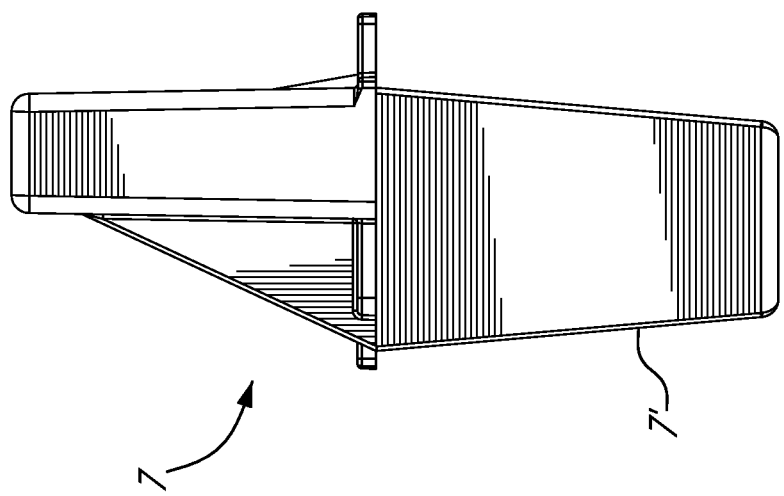
FIG. 3E is a left side view of the exemplary claw used to engage the thumb rest of the syringe piston.
Figure 3D:
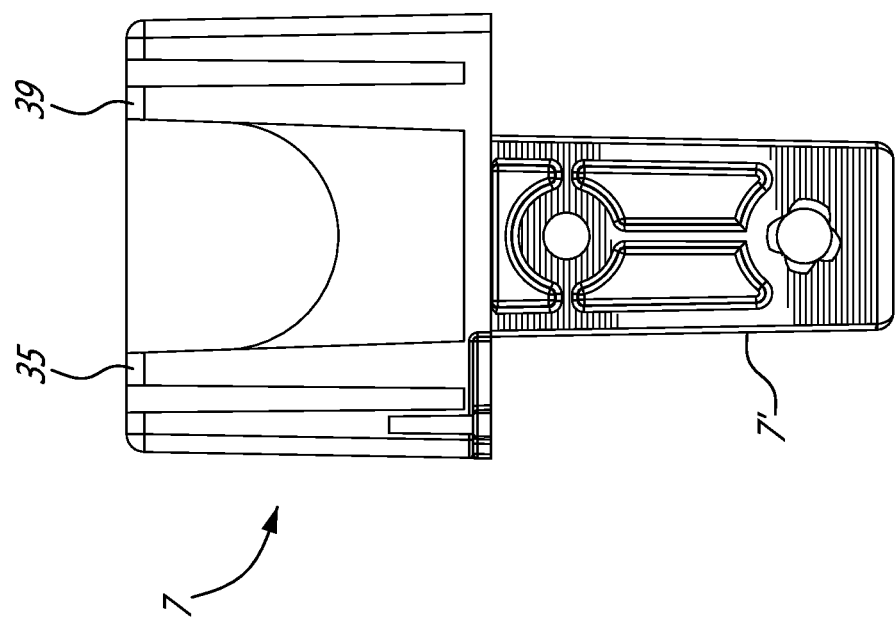
FIG. 3D is a front view of an exemplary claw used to engage a thumb rest of a syringe piston in accordance with the present invention.

As particularly shown in FIGS. 1, 2 and 3, the claw 7 can be in the shape of a plate that is adapted to fit in the channel 27 and slide therein while positioned perpendicular to the channel 27. The claw 7 may comprise a leg 7', which downwardly extends from the bottom of the claw 7 and extends all the way to the casing 5 through or in the slot 31 to provide the mechanical connection. The claw 7 shown on FIGS. 3A to 3C comprises a socket 8 to receive a driving peg 42 from within the casing 5 to ensure the mechanical connection, as exemplified on FIG. 4. The driving peg 42 may be maintained in the claw 7 using a pin or screw (not shown) inserted through channel 32. The claw 7 is also formed with a pair of oppositely disposed wings 35, 37 having respective inwardly turned flanges 39, 41 adapted to engage the thumb rest 9 of the piston rod 17 as shown in FIG. 1. When the thumb rest 9 is engaged in the wings 35, 37 of the claw 7 and the slides in the channel 27, the piston extends into or retracts out of the hollow barrel 11. The casing 5 may provide sealing rubber strips (not shown) along the slot 31 on one or both sides thereof to be in contact with the claw's 7 leg or the driving peg 42 to isolate interior of the casing 5. Alternatively, or in addition, the casing 5 may also comprise a first rubber-encased spring in the slot 31 between an outer end of the casing 5 and the claw 7 and a second rubber-encased spring in the slot 31 between the claw 7 and the inner end 30 to isolate the interior of the casing 5. In addition, in order to hold pistons and thumb rests of various diameters, the flanges 39, 41 may be inwardly slopped as shown in FIG. 3.

Figure 4C:
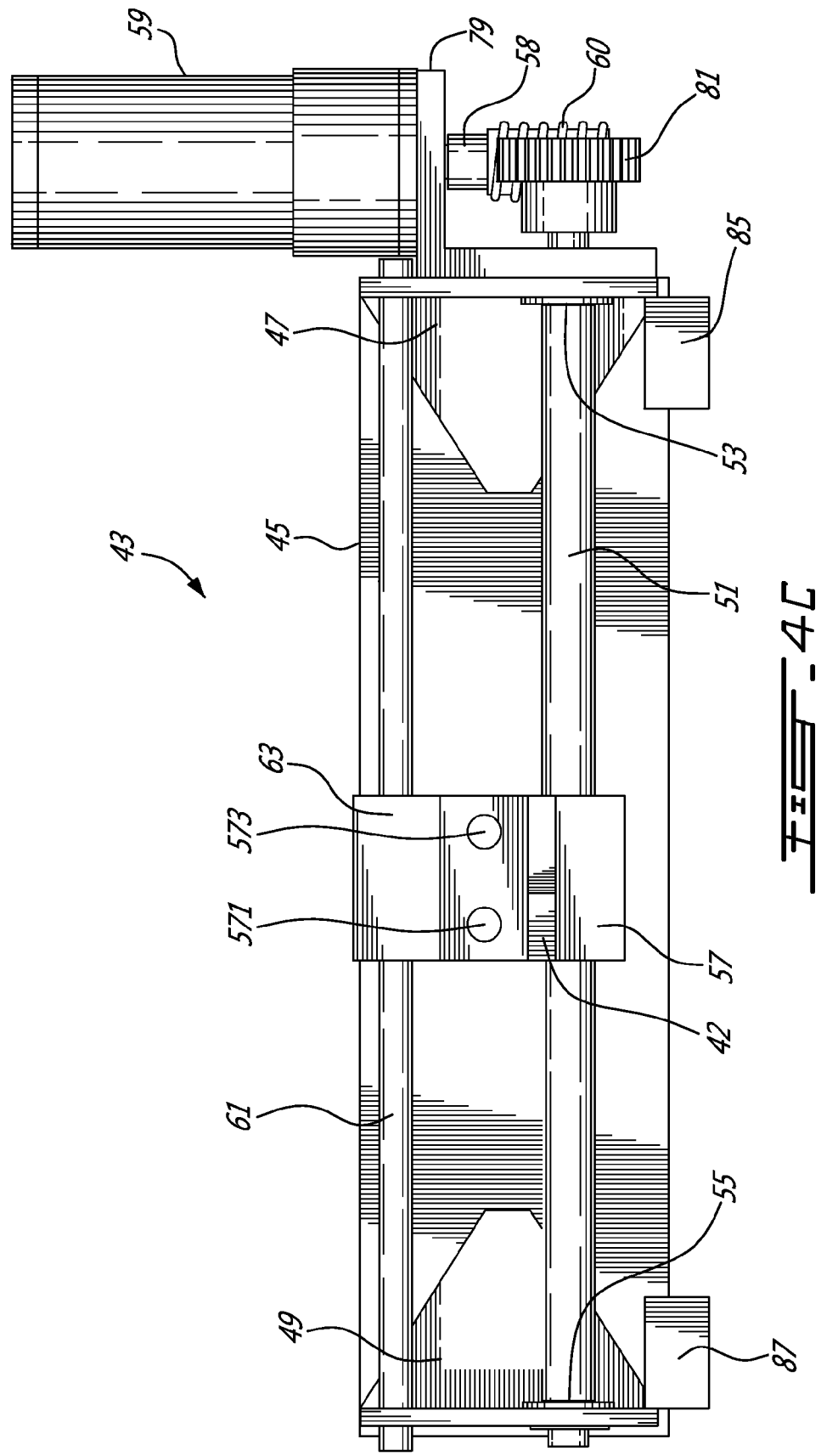
FIG. 4C is a top view the exemplary mechanical assembly of the exemplary device according to the invention, FIGS. 4A, 4B and 4C being referred together as FIG. 4.
Figure 7:
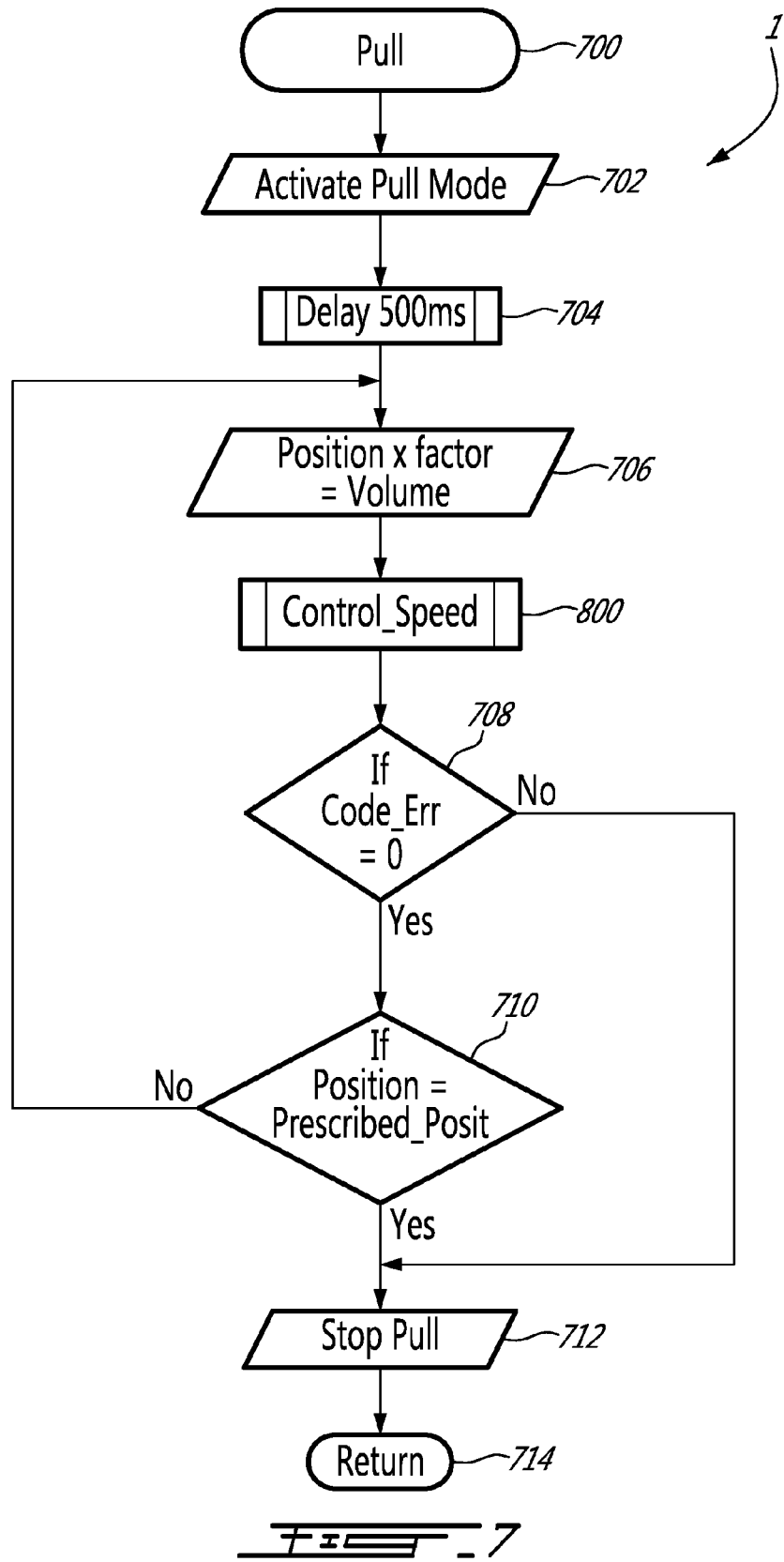
FIG. 7 is a flowchart of an exemplary method to control a pull movement in accordance with the present invention.
Figure 8:
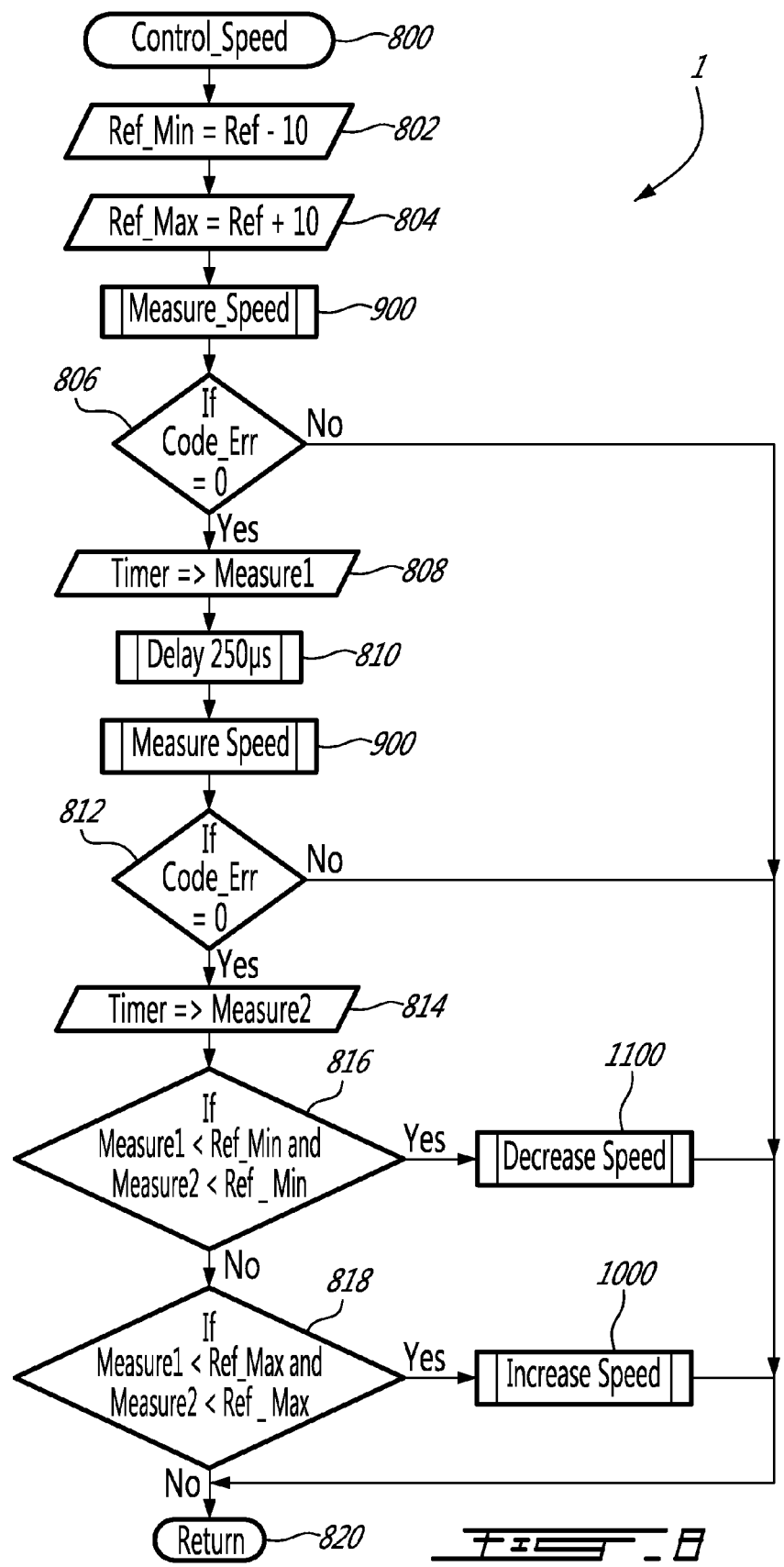
FIG. 8 is a flowchart of an exemplary method to control speed in accordance with the present invention.
Figure 9:
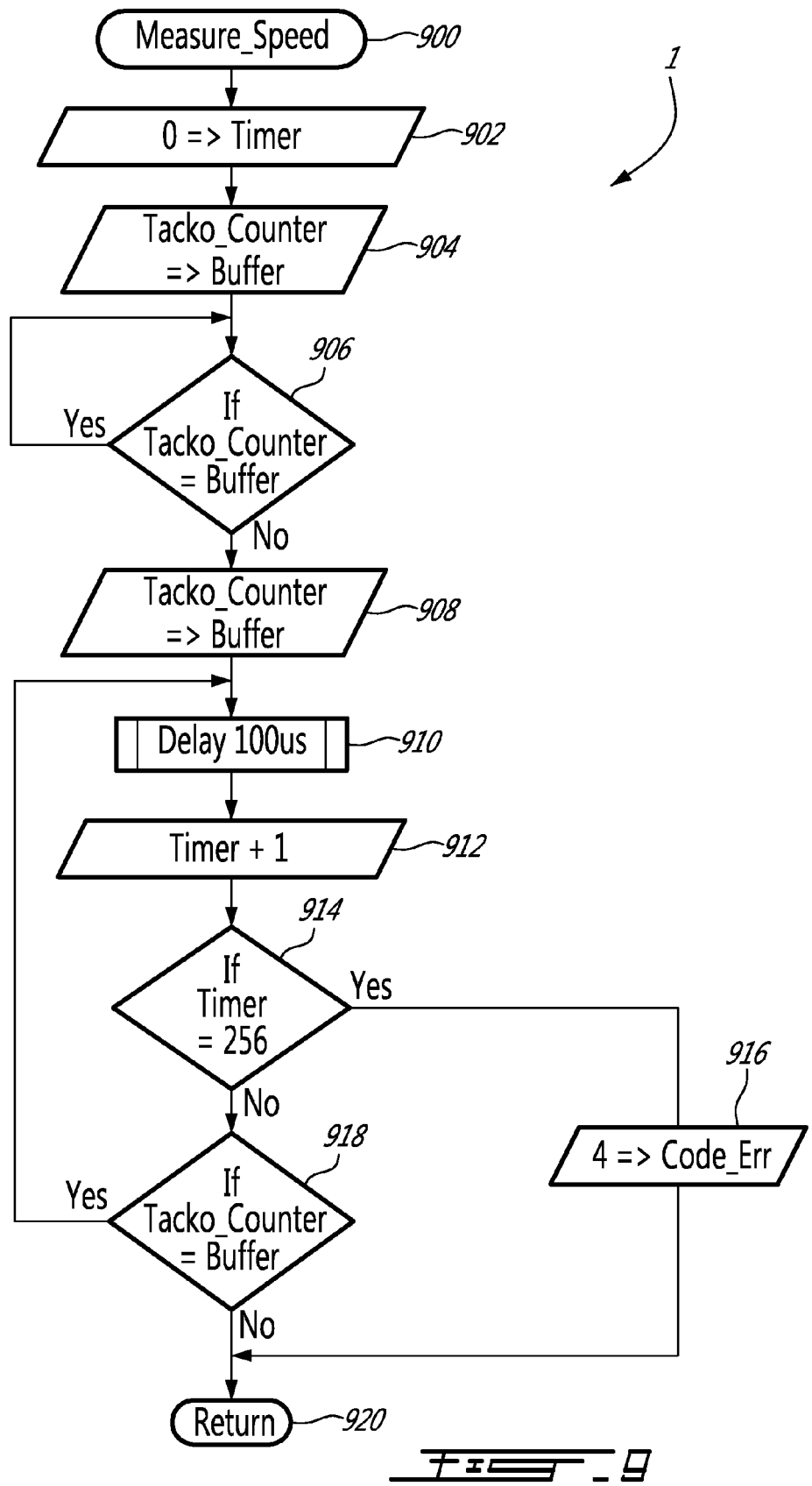
FIG. 9 is a flowchart of an exemplary method to measure speed in accordance with the present invention.

FIG. 4 shows an exemplary mechanical assembly of the exemplary device 1. The casing 5 is a generally hollow structure that contains various equipments required to actuate the syringe's 3 piston in accordance with the present invention. Therefore, inside the casing 5, there is provided a rigid structure 43 which is schematically illustrated in FIG. 4. The structure 43 is shown with a base 45 and two opposed vertical partitions 47, 49 respectively disposed at both ends of base 45 Skilled readers will readily recognize that 45, 47 and 49 could be provided in multiple different pieces as shown or in a single piece (not shown) without affecting the present invention.

Between the uppermost portions of the vertical partitions 47, 49, a lead screw 51 is mounted as shown in FIG. 4 parallel to the slot 31. The lead screw 51 may be supported at both ends respectively by means of ball bearings 53, 55 as shown on FIG. 4. The lead screw 51 rotates upon being induced into rotation by means of a motor 59. A flange nut assembly 57 is mounted as illustrated in FIG. 4 over the lead screw 51 to move therealong in either direction, depending on the direction of rotation of the lead screw 51. It should be noted the device 1 illustrated in this exemplary embodiment ensures that the flange nut assembly 57 moves along the lead screw 51 without itself being rotated by means of a monitoring rod 61 Skilled readers will recognize that other means could be used to achieve the same purpose (including, for instance, relying of the slot 31 to ensure stability).

The monitoring rod 61, if present, may be mounted in known manner between the vertical partitions 47 and 49, parallel to the lead screw 51. The monitoring rod 61 is shown in a similar horizontal plane as the lead screw 51, but it could also be located below the lead screw 51 (not shown) while still achieving stabilization of the flange nut assembly 57, once properly adapted. The driving peg 42 is attached to the flange nut assembly 57 using, for example, screws 571, 573. In the illustrated exemplary embodiment, the flange nut assembly 57 moves along the lead screw 51 without rotation, which will move the driving peg 42 to carry the claw 7, which will in turn engage the piston rod 17 in and out of the hollow barrel 11.

As indicated above, the lead screw 51 can rotate in either direction through the motor 59. The motor 59 in the exemplary embodiment of FIG. 4 can operate in both directions. Provided with a necessary transmission means (not shown), skilled reader will recognize that it would also be possible to use a one-way motor to operate the lead screw 51 in both directions. The motor 59 is likely to be provided with an encoder (not illustrated) known to a skilled artisan to measure rotations of the motor 59, which in turn enables measurement of the piston rod 17 movements.

In the exemplary embodiment of FIG. 4, the motor 59 has a shaft 58 inserted into a worm screw 60. An exemplary L-shaped bracket 79 is provided to fix the motor 59 to the vertical partition 47. A spur gear 81 is mounted on the lead screw 51 to mesh with the worm gear 60, so that when the motor 59 is in operation, the lead screw 51 will rotate through the cooperation of the worm gear 60 with the spur gear 81. The skilled reader will appreciate that other embodiments could provide direct drive between the motor 59 and the lead screw 51 (not shown) or could provide parallel mount of the motor 59 and the lead screw 51 using conventional gears (not shown) without affecting the present invention.

Various sensors may also be associated with the device 1 in accordance with the present invention. These sensors may provide information used to determine, for instance, whether there is a syringe 3 in the device 1, what volume is the currently inserted syringe 3 and if the syringe 3 is well placed therein. They could also indicate when maximum displacement of the piston rod 17 is reached. For instance, exemplary sensors 82, 83, shown on FIG. 2, may be used to detect presence of a syringe 3 and may also further be used to determine its caliber (e.g., 30 or 60 ml). Only the sensor 82 is shown on the curved cut out portion 21, but skilled reader will readily recognize that the sensor 82 and/or another sensor (not shown) could be located on curved cut out portions 23. Likewise, more than one sensor 83 could also be used without affecting the present invention.

A sensor 85, as shown of FIG. 4, may be used to detect a position of maximum insertion of the piston (e.g., volume set at zero) and may also used to calibrate the positioning system. One or more sensor 87 may also be used to prevent a complete exit of the piston. The one or more sensor 87 may be positioned in view of the different lengths of the piston rod 17 expected to be used in the device 1.

A flip-flop button 75 may be provided to trigger manual, automatic or default operation of the device 1. For instance, actuating the flip-flop button 75 may engage the piston rod 17 in the hollow barrel 11 in a corresponding direction. The flip-flop button 75 may also be used to initiate the activation of one of the automatic options, for instance, if they have previously been selected in the menu.

The exemplary casing 5 may also comprises a keyboard 77, which can be used to program or control the device 1 and a visual display unit 79 that can be used to monitor its operation. Visual signals may be provided via the visual display unit 79 to indicate if the syringe 3 can be inserted or removed from the casing 5 (e.g., using one or more LED and/or an LCD panel (not shown)). It should be noted that the visual display unit 79 may also show when it is possible to operate the device 1. While the LCD panel may provide textual information to the user, color codes may also be sued on the visual display 79, for instance, as follows:

green: when the color is fixed, the syringe 3 can be inserted or removed;
twinkling yellow: the device 1 awaits the input of a command or an action;
red: the device is in operation (syringe 3 not to be removed or inserted);
twinkling red: an error took place (e.g., reset is required).

The LCD panel (not shown) also associated with the visual display unit 79 may show quantity of solution inside the syringe 3. It will also be used to output certain data, such as charge status of a battery, current mode of operation, current liquid intake, menu options, etc.

The keyboard 77 may be used to enter various options or to specify a given volume of liquid. A menu button, enter button and arrows are shown as input means of the keyboard 77 on the exemplary embodiment of FIGS. 1 and 2. Conventional letters and/or numbered keys may also be provided (not shown), in addition or replacement of shown keys, without affecting the present invention.

Exemplary options of the device 1 are not limited to the following list, but may include:
automatic intake of a predetermined volume (e.g., given quantity (cc or ml), shown on the visual display unit 79, triggered by action of the flip-flop button 75);
default intake of a predetermined volume (e.g., given quantity (cc or ml), not shown on the visual display unit 79, triggered by action of the flip-flop button 75);
automatic intake of a predetermined volume, N times;
default intake of a predetermined volume, N times;
thrust of current intake;
automatic thrust of a predetermined volume (e.g., given quantity (cc or ml), shown on the visual display unit 79, triggered by action of the flip-flop button 75);
thrust of a default volume (e.g., given quantity (cc or ml), not shown on the visual display unit 79, triggered by action of the flip-flop button 75);
automatic thrust of a predetermined volume, N times;
thrust of a default volume, N times;
inlet of a volume which will automatically be subdivided into a plurality of volumes corresponding to sequentially inserted or prescribed syringes 3 (e.g., may calculate the number of syringes to reach the predetermined quantity, or subtracts volume from sequentially inserted syringes until the desired volume is reached; may further indicate and instruct to insert or remove the syringes; can make it possible to decide whether the volume selected will be transferred by means of a single syringe or with a plurality of syringes, etc.);
multiple dose production: intake of a given volume for producing multiple doses followed by a request for entering a desired volume per dose. The number of doses is then calculated and the doses are thereafter expelled from the given volume.

It should be noted that a manual mode may also be provided, in which the visual display unit 79 may show the volume currently extracted or expelled, thereby diminishing the likelihood of mistakes.

A button, toggle or otherwise, (not shown) may be used to turn the device 1 on and off and may further be used as a reset button as it is well known to those skilled in the art. This button should be located on the device 1 where it is not too cumbersome.

A battery (not shown) may also be provided in the casing 5 for operation of the device 1. Alternatively, a port (not shown) on the casing 5 may be used to provide power to the device 1.

The port (not shown) on the casing 5 may be present even if the device 1 is battery operated to allow charging the battery. The same or different port (not shown) may further be provided to interface with a computer.

With respect to the electronic parts of the device 1, control may be carried out by use of microcontrollers. For instance, one microcontroller could be associated with the LCD display and to the keyboard 77, and another one associated to the motor 59 and the exemplary sensors 82, 83, 85, 87 of the device 1. A memory unit (not shown) may also be used to preserve data. Communication between the microcontrollers and the memory may be made, for instance, by means of the Inter Integrated Circuit ($I^2C$) protocol.

A position sensor, such as an accelerometer, (not shown) could also be provided to determine orientation of the device 1, which information may shown to the user and may further be used in operation of the device 1.

FIG. 5 shows an exemplary electronic controller module 800 for controlling displacement of a syringe piston within a syringe that comprises a hollow barrel to contain a fluid. The syringe piston is slidably engaged in the hollow barrel. The electronic controller 800 causes an outward movement of the syringe piston within the barrel. The electronic controller module 800 comprises an input/output port 840 and a processor module 810. The processor module 810 is used for determining a prescribed speed of the outward movement. The processor module 810 sends an initial motor command via the output port 840 to activate a motor at an initial motor speed. The motor is operatively connected to the syringe piston to cause the outward movement. The input port 840 receives speed measurements. The prescribed speed and the speed measurements may be stored in a memory module 820 of the electronic controller module 800.

The processor module 810 thereafter attempts to match the prescribed speed based on the speed measurements by sending successive further motor commands via the output port 840. Each further motor command comprises a further motor speed. The electronic controller module 800 is within a hand-held syringe control system.

A prescribed end position of the outward movement may also be stored in the memory unit 820. The input port 840 may also further receive position measurements of the syringe piston. The processor module 810 may thus send a final motor command via the output port 840 to stop the motor once at least one of the position measurements matches the prescribed end position. The processor module 840 may be able to divide the prescribed speed by a factor (e.g., reduce speed by two-fold) once at least one of the position measurements is within a range from the prescribed end position. The prescribed speed and/or the prescribed end position may be received via from a key port 850.

The processor module 810 may further receive a command to cause an inward movement of the syringe piston within the barrel. The processor module 810 thus sends an inward motor command via the output port 840 to activate the motor at an inward motor speed. The motor is operatively connected to the syringe piston to cause the inward movement. The processor module 810 also sends a stop motor command via the output port 840 once at least one of the position measurements matches an empty position.

The processor module 810 may represent a single processor with one or more processor cores or an array of processors, each comprising one or more processor cores. The processor module 810 may further be a general purpose processor or a specific microcontroller programmed in accordance herewith. The memory module 820 may comprise various types of memory (different standardized or kinds of Random Access Memory (RAM) modules, memory cards, Read-Only Memory (ROM) modules, programmable ROM, etc.).

The input/output port 840 represents at least one physical interface that can be used to communicate with other modules. The input/output port 840 may be made visible to the other modules through one or more logical interfaces. The variants of processor module 810, memory module 820 and input/output port 840 usable in the context of the present invention will be readily apparent to persons skilled in the art. Likewise, even though explicit mentions of the memory module 820 and/or the processor module 810 are not made throughout the description of the present examples, persons skilled in the art will readily recognize that such modules are used in conjunction with other modules of the electronic controller module 800 to perform routine as well as innovative steps related to the present invention.

FIGS. 6 to 11 show different flowcharts of exemplary methods to control the device 1 in accordance with the present invention. In the example of FIGS. 6 to 11, a movement 600 of the syringe's piston is initiated. The movement 600 may be the result, for instance, of pressing the flip-flop button 75 in one direction or another, or otherwise by activation of a program of the device 1. The movement 600 also provides a prescribed position (or prescribed_posit) to be attained. Thereafter, a flag (e.g., flag_movement) may be toggled 602 (e.g., from 0 to 1 or set to 1). It is then determined if the prescribed position is smaller or greater than a current position 604. If the prescribed position is smaller than the current position, then a push movement 606 is initiated. If the prescribed position is greater than the current position, then a pull movement 700 is initiated, as will be shown in more detail with reference to FIG. 7. Following return from either push 606 or pull 700, a new position is stored in memory. The flag (e.g., flag_movement) may then be toggled again 610 (e.g., from 1 to 0 or set to 0). The movement 600 being completed, the exemplary method of FIG. 6 returns 612.

The pull movement 700 may first be activated 702 by, for instance, setting a flag (e.g., from 0 to 1 or set to 1) thereby starting the motor 59 in the proper direction for the pull movement 700. A delay (e.g., 500 ms) 704 may be triggered, which can be useful, for instance, for ensuring that the motor 59 has enough time to properly initiate the movement and as a means to avoid sending speed correction commands too early. A volume currently loaded in the syringe is then a calculated 706. One way to obtain such volume is to associate a factor between position and volume for each supported type of syringe. The current position may then be multiplied by the factor to obtain the volume. The calculated volume and other information (e.g., from the flags) may be presented or updated (not shown) at multiple times during the various routines, e.g., on the LCD screen. Speed of the movement 600 is thereafter controlled 800, which will be detailed with reference to FIG. 8. If return from the control speed 800 shows an error 708, the pull movement 700 is stopped (the flag may further be toggled 712) and control is returned 714 to the calling method (in this example the movement 600). If the return from the control speed 800 shows no error 708, then the current position is compared to the prescribed position. If there is a match 710, then the pull movement 700 is stopped (the flag may further be toggled 712) and control is returned 714 to the calling method (in this example the movement 600). If there is no match 710 between the prescribed position and the current position, then the methods loops and may re-measure the volume 706 before activating again the control speed method 800. The pull movement 700 being detailed on FIG. 7, the pull movement 606, for the sake of conciseness, is not explicitly detailed.

The control speed method 800 may start by setting boundary upper and lower time measurements 802 and 804 compared to respective reference time values. Current speed is then measured 900 by means of a timer value, which will be detailed with reference to FIG. 9. If return from the measure speed 900 shows an error 806, control is returned 820 to the calling method (in this example the pull movement 700). Otherwise, the timer value (set by the measure speed method 900 as will be shown further below) is stored as a first time measure 808. Following a delay (e.g., 250 μs) 810, the measure speed method 900 is called again. If return from the measure speed 900 shows an error 812, control is returned 820 to the calling method (in this example the pull movement 700). Otherwise, the timer value (set by the measure speed method 900) is then stored as a second time measure 814. Comparison is then made between the two measures and the minimal reference value. While a single time measure could be taken and compared, using two time measures as shown in the exemplary method 800 ensures greater reliability. If both time measures are below the minimal time reference value (i.e., displacement took less time than the minimal reference time), then a decrease speed method 1100 is called, which will be detailed with reference to FIG. 10. If both time measures are above a maximal reference value (i.e., displacement took more time than the maximum reference time), then an increase speed method 1000 is called, which will be detailed with reference to FIG. 11. Control is thereafter returned 820 to the calling method (in this example the pull movement 700).

The measure speed method 900 starts by resetting the timer value (e.g., setting the timer to 0). A tachometer counter, that stores a value representing received and counted pulse signals indicating motor 59 rotations, is then buffered 904. In the present example, the motor sends 12 pulse signals per rotation. As soon as the tachometer counter changes (e.g., when motor 59 rotates by more than 30 degrees), and becomes different than the buffered value 906, a new value of the tachometer counter is buffer again 908. 904 and 906 are exemplary steps that may be executed to ensure that measurement systematically starts at the same moment compared to the last received pulse signal. It should be noted that further means (e.g., a decremented variable) may be used to ensure that the loop 906 is executed only a maximum number of times (not shown) before generating an error (not shown), thereby preventing an endless loop.

Once the new value is buffered 908, a delay (e.g., 100 μs) 910 is followed by an increment of the timer value 912. If the incremented timer value equals 256 (or another high value determined by experimentation), it means that loop initiated in 918 has been executed too often to represent a reasonable measurement. An error is thus generated and control is returned 920 to the calling method (in this case, the control speed method 800). Otherwise, if the tachometer counter is equal to the buffer (e.g., as long as the motor 59 does not rotate by at least 30 degrees) 918, the loop returns to the delay 910. Once the tachometer counter changes (e.g., when motor 59 rotates by at least 30 degrees), control is returned 920 to the calling method (in this case, the control speed method 800). The timer value, in the example of FIG. 9, thus represents the number of delay 910 incurred between two pulse signals from the motor 59 (in the present example by the rotation of at least 30 degrees, i.e., N times 100 μs).

Skilled readers will readily recognize that measuring time, e.g., with timer values, and comparing time measurements with reference time values is equivalent to measuring speeds and comparing measured speed to prescribed or reference speeds.

The increment speed method 1000 and the decrease speed method 1100 both control an output value that represents speed of the motor 59. The output value may be a pulse-width modulation (PWM) value ranging, in the example of FIGS. 10 and 11, from 0 to 15, with 0 being constantly powered and 15 being minimally powered. In practice, exemplary values from 1 to 12 are used to provide meaningful motor 59 speeds, with 1 being maximum speed and 12 being minimal speed.

Figure 10:
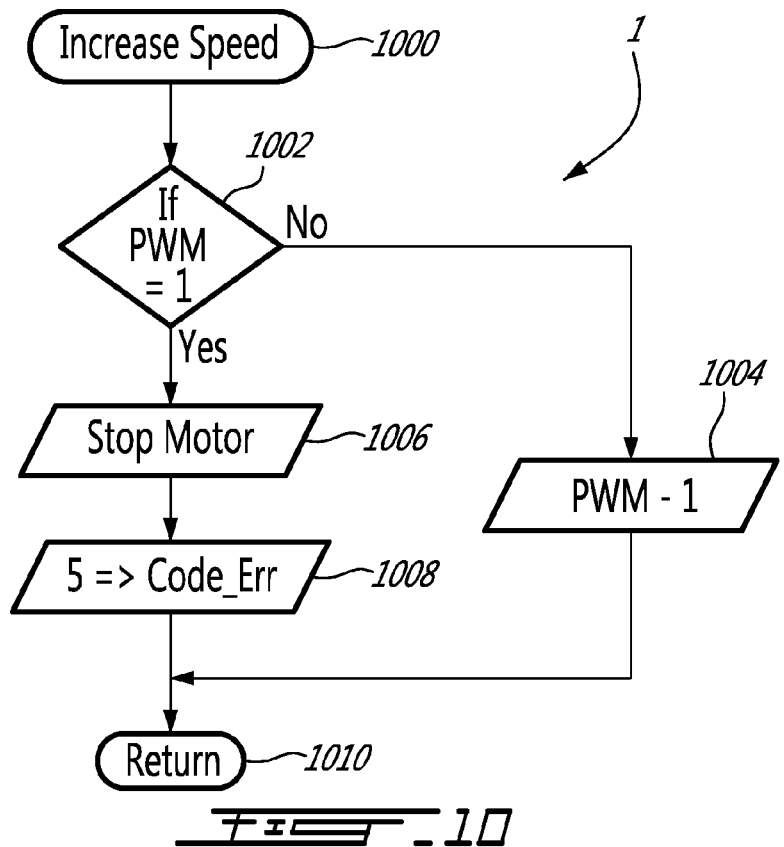
FIG. 10 is a flowchart of an exemplary method to increase speed in accordance with the present invention.
Figure 11:
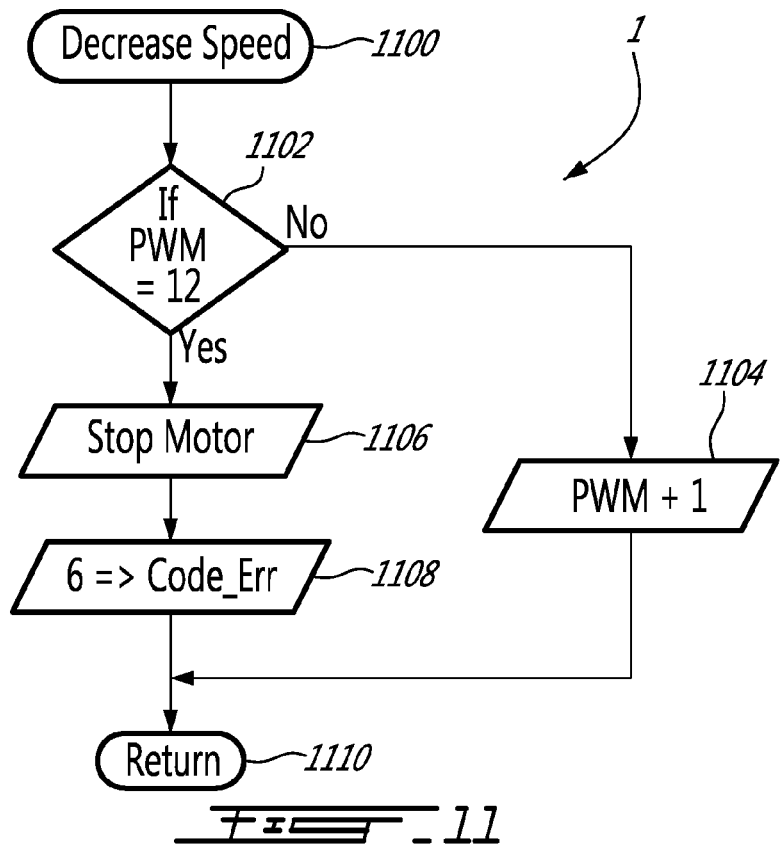
FIG. 11 is a flowchart of an exemplary method to decrease speed in accordance with the present invention.

Considering these exemplary values relevant to the examples of FIGS. 10 and 11, the increase speed method 1000 begins with verifying 1002 if output value represents maximum speed (e.g., 1). If not, the output value is updated to increase speed, in the present example, by decrementing the output value by 1. Control is then returned 1010 to the calling method (in this case, the control speed method 800). Otherwise, if output value represents maximum speed, the motor 59 is stopped 1006, an error is generated 1008 and control is returned 1010 to the calling method (in this case, the control speed method 800).

Similarly, the decrease speed method 1100 begins with verifying 1102 if output value represents minimum speed (e.g., 12). If not, the output value is updated to decrease speed, in the present example, by incrementing the output value by 1. Control is then returned 1110 to the calling method (in this case, the control speed method 800). Otherwise, if output value represents minimum speed, the motor 59 is stopped 1106, an error is generated 1108 and control is returned 1110 to the calling method (in this case, the control speed method 800).

If control is returned by one or more of the methods 600-1100 because of a generated error, specific display relative to the error may further be shown on the device 1.

It is contemplated that all the parts that constitute the device 1 according to the present invention as described with respect to the preferred embodiment be of a minimum weight to execute movement of the piston with sufficient power. Volumic mass or maximum dynamic viscosity values should be established to define the nature of the substances that can be used with this device. The maximum power of the mechanical system should be one that exceeds the above values thereby ensuring a reasonable lifespan to the device 1.

A method is generally conceived to be a self-consistent sequence of steps leading to a desired result. These steps require physical manipulations of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities. The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses. In the drawings, like elements are represented by the same reference numerals. Drawings are not necessarily drawn to scale.

What is claimed is:

1. An electronic controller module for controlling displacement of a syringe piston within a syringe that comprises a hollow barrel to contain a fluid, the syringe piston being slidably engaged in the hollow barrel, wherein the electronic controller causes an outward movement of the syringe piston within the barrel, the electronic controller module comprising:
   an output port;
   a processor module for determining a prescribed speed of the outward movement of the syringe piston, wherein the processor module:
      sends an initial motor command via the output port to activate a motor at an initial motor speed, wherein the motor is operatively connected to the syringe piston to cause the outward movement;
   an input port that receives speed measurements;
   wherein the processor module attempts to match the prescribed speed based on the speed measurements by sending successive further motor commands via the output port, each further motor command comprising a further motor speed; and
   wherein the electronic controller module is within a handheld syringe control system.

2. The electronic controller module of claim 1, wherein the prescribed speed and the speed measurements are stored in a memory module.

3. The electronic controller module of claim 1, wherein the handheld syringe control system is battery operated in a sterile environment.

4. The electronic controller module of claim 1, wherein the processor module receives the prescribed speed from a key port.

5. The electronic controller module of claim 1, wherein a prescribed end position of the outward movement is stored in a memory unit, the input port further receiving position measurements of the syringe piston, wherein the processor module sends a final motor command via the output port to stop the motor once at least one of the position measurements matches the prescribed end position.

6. The electronic controller module of claim 5, wherein the processor module reduces the prescribed speed once at least one of the position measurements is within a range from the prescribed end position.

7. The electronic controller module of claim 5, wherein the processor module further receives a command to cause an inward movement of the syringe piston within the barrel, wherein the processor module:
   sends an inward motor command via the output port to activate the motor at an inward motor speed, wherein the motor is operatively connected to the syringe piston to cause the inward movement; and
   sends a stop motor command via the output port once at least one of the position measurements matches an empty position.

8. The electronic controller module of claim 1, wherein the handheld syringe control system comprises:
   a handheld outer casing;
   a finger flange retainer formed exteriorly of the casing to fixedly engage a finger flange of the syringe; and
   a thumb rest retainer slidably movable on a first axis relative to the outer casing and adapted to engage a thumb rest of the syringe, the motor being operatively connected to the syringe piston via the thumb rest retainer to cause the fluid to enter the hollow barrel.

9. The electronic controller module of claim 8, wherein the handheld syringe control system is adapted to receive syringes of various diameters and comprises an elongated circular recess formed at one end thereof.

10. The electronic controller module of claim 9, wherein the elongated circular recess includes a pair of oppositely disposed curved cut out portions adapted to permit a syringe with a hollow barrel of larger diameter to sit in the elongated circular recess.

11. The electronic controller module of claim 9, wherein the finger flange retainer comprises a transverse slit formed in the outer casing at an inner end of the elongated circular recess and adapted for insertion of the finger flange therein to fix the syringe relative to the outer casing, wherein the handheld outer casing is formed with a longitudinal channel along the first axis which extends to the inner end of the elongated circular recess, a slot being formed at the bottom of the longitudinal channel and extending along the first axis.

12. The electronic controller module of claim 11, wherein the thumb rest retainer comprises a claw adapted to engageably receive the thumb rest, the claw slidably engaged in the longitudinal channel, and operatively connected to the mechanical driver, wherein the claw is shaped as a plate having a pair of oppositely disposed holding wings to receive and hold the thumb rest, wherein the wings are inwardly beveled to hold pistons and thumb rests of various diameters.

13. The electronic controller module of claim 12, wherein the claw comprises a leg downwardly extending from a bottom portion of the claw and centrally thereof, the leg extending through the slot to connect with the mechanical driver, or wherein the mechanical driver comprises a shaft extending upwardly through the slot to connect with the claw.

14. The electronic controller module of claim 1, wherein the handheld syringe control system provides a rigid structure, a lead screw mounted within the rigid structure in alignment with a first axis, a claw mounted over the lead screw to move therealong without rotation relative to the rigid structure as the lead screw is rotated, the claw providing a thumb rest retainer, wherein the lead screw is operatively connected to the motor through at least one gear.

15. The electronic controller module of claim 1, wherein the wherein the handheld syringe control system comprises a lead screw in alignment with a first axis, wherein a thumb rest retainer is connected to the lead screw to move therealong without rotation relative to the outer casing as the lead screw is rotated, wherein the lead screw is operatively connected to the motor through at least one gear, a shaft of the motor being inserted into a worm screw, a spur gear being fixedly mounted at one end of the lead screw, the spur gear meshing with the worm screw to operate the lead screw.

16. The electronic controller module of claim 14, wherein the rigid structure supports a monitoring rod parallel to the lead screw, wherein the claw is engaged over the monitoring rod to prevent rotation thereof when the lead screw is rotated, wherein the lead screw is mounted on the rigid structure by a pair of ball bearings supported at both ends of the lead screw.

17. The electronic controller module of claim 14, wherein the rigid structure has an inner end wall and an outer end wall, the lead screw being mounted on top of the inner end wall and the outer end wall through ball bearings, the inner end wall being disposed to allow for calibrating the syringe at a zero value, and the outer end wall being disposed to prevent the piston from movably extending outside the hollow barrel.

* * * * *